(12) United States Patent
Matsumoto et al.

(10) Patent No.: US 8,608,670 B2
(45) Date of Patent: Dec. 17, 2013

(54) GUIDEWIRE

(75) Inventors: Satoru Matsumoto, Aichi (JP); Masayuki Takahashi, Aichi (JP)

(73) Assignee: Asahi Intecc Co., Ltd., Aichi (JP)

( * ) Notice: Subject to any disclaimer, the term of this patent is extended or adjusted under 35 U.S.C. 154(b) by 382 days.

(21) Appl. No.: 12/977,121

(22) Filed: Dec. 23, 2010

(65) Prior Publication Data
US 2011/0160703 A1   Jun. 30, 2011

(30) Foreign Application Priority Data
Dec. 25, 2009   (JP) ................. 2009-294688

(51) Int. Cl.
*A61B 5/00*   (2006.01)

(52) U.S. Cl.
USPC ........................................ 600/585

(58) Field of Classification Search
USPC ........................................ 600/585
See application file for complete search history.

(56) References Cited

U.S. PATENT DOCUMENTS

| | | |
|---|---|---|
| 5,063,935 A | 11/1991 | Gambale |
| 5,345,945 A | 9/1994 | Hodgson et al. |
| 5,365,942 A | 11/1994 | Shank |
| 5,678,296 A | 10/1997 | Fleischhacker et al. |
| 5,957,903 A | 9/1999 | Mirzaee et al. |
| 7,077,811 B2 | 7/2006 | Vrba et al. |
| 7,399,283 B2 | 7/2008 | Kato |
| 2002/0151823 A1 | 10/2002 | Miyata et al. |
| 2004/0116833 A1 | 6/2004 | Kato et al. |
| 2005/0154371 A1 | 7/2005 | Miyata et al. |
| 2006/0041204 A1 | 2/2006 | Kato |
| 2006/0235337 A1 | 10/2006 | Vrba et al. |
| 2008/0214959 A1 | 9/2008 | Miyata et al. |

FOREIGN PATENT DOCUMENTS

| | | |
|---|---|---|
| CN | 1939551 A | 4/2007 |
| EP | 0495299 A1 | 7/1992 |
| JP | 6501179 T | 2/1994 |
| JP | 08-173547 A | 7/1996 |
| JP | 09-056822 A | 3/1997 |
| JP | 2003052831 A | 2/2003 |
| JP | 2004190167 A | 7/2004 |
| JP | 2005103171 A | 4/2005 |
| JP | 2005185386 A | 7/2005 |
| JP | 2006511304 A | 4/2006 |
| JP | 2006158737 A | 6/2006 |
| JP | 2008161491 A | 7/2008 |
| WO | 20051014095 A1 | 2/2005 |

OTHER PUBLICATIONS

JP2009-294688 Notice of Reasons for Rejection mailed Nov. 28, 2011.
Extended EP Search Report for EP10196565.5 dated Dec. 7, 2011.
First Office Action issued on Jun. 19, 2012 by the Chinese Patent Office in corresponding Chinese Application No. 20121061400756840, with English translation.
Second Office Action issued on Oct. 23, 2012 by the Chinese Patent Office in corresponding Chinese Application No. 2012101800772160, with English translation.

*Primary Examiner* — Max Hindenburg
(74) *Attorney, Agent, or Firm* — Lowe Hauptman & Ham, LLP (57) ABSTRACT

An object of the present invention is to provide a guidewire having high safety and improved flexibility and rotation followability, and capable of directing a catheter with ease. A guidewire of the present invention has an inner coil that surrounds a distal side portion of a core shaft, and an outer coil that surrounds the inner coil and the distal side portion of the core shaft. The core shaft has a second flat part in flattened shape in substantially contact with an inner peripheral surface of the inner coil. With this configuration, the distal side portion of the guidewire is protected by a double coil structure, while having high torsional stiffness. This leads to improvement in safety and rotation followability, while allowing a catheter to be directed with ease.

2 Claims, 8 Drawing Sheets

GUIDEWIRE

CROSS REFERENCE TO RELATED APPLICATIONS

This application is based on Japanese Patent Application No. 2009-294688 filed with the Japan Patent Office on Dec. 25, 2009, the entire content of which is hereby incorporated by reference.

TECHNICAL FIELD

The present invention relates to a medical guidewire.

BACKGROUND ART

There have conventionally been proposed a variety of medical guidewires for guiding, for example, a catheter which is used by being inserted into tubular organs such as blood vessels, digestive tracts, and ureters, and intracorporeal tissues for treatment or test. The guidewires include those with a structure where a double coil is provided at a distal portion of a core shaft (e.g., see Japanese Translation of PCT Publication Nos. 6-501179 and 2006-511304), those using a stranded wire made up of a plurality of strands inside a coil (e.g., see Japanese Patent Application Laid-Open No. 2008-161491), and those provided with a flat portion at the tip of a core shaft (e.g., see Japanese Patent Application Laid-Open No. 2005-103171).

Generally, the guidewire is required to have flexibility on the front side (distal side) of the guidewire and rotation followability to transmit a rotation performed by an operator from the rear side (proximal side) to the front side of the guidewire.

SUMMARY OF INVENTION

In recent years, the area of use of the guidewire tends to be expanding. The guidewire has come to be used in more peripheral-side blood vessels in a heart, blood vessels in a brain, and the like. For this reason, the guidewire has been required to have higher safety, and further flexibility and rotation followability.

Especially, the blood vessel in the brain is a highly delicate portion. It is thereby required not only to prevent damage of the blood vessel and a tissue surrounding the vessel, but also to have high rotation followability.

Further, a guidewire for the brain is required to guide a microcatheter into an aneurysm, having occurred in a tortuous blood vessel, by passing through the blood vessel and then changing a direction of the microcatheter to a direction where the aneurysm is present. It can be considered that a torsional stiffness of the tip portion of the guidewire is made high for the purpose of easily changing the direction of the catheter. However, it has been difficult to make such a tip portion with high torsional stiffness have a structure formed in view of the safety in combination with the flexibility.

The present invention has been made in view of such circumstances. An object of the present invention is to provide a guidewire having high safety and improved flexibility and rotation followability, while being able to direct a catheter with ease.

In the present invention, the above object is achieved by the structure listed below.

A guidewire in accordance with the present invention includes: a core shaft; an inner coil that is formed by winding at least one strand, and surrounds a distal side portion of the core shaft; an outer coil that is formed by winding at least one strand, and surrounds the inner coil and the distal side portion of the core shaft; a flat part in flattened shape, which is provided in the distal side portion of the core shaft, expands in width toward a distal end of the distal side portion, and is in contact with an inner peripheral surface of the inner coil at least at the distal end of the distal side portion; a tip joint that joins a front end of the outer coil and a front end of the inner coil to a distal end of the flat part of the core shaft; an outer rear end joint that joins a rear end of the outer coil to the core shaft; and an inner rear end joint that joins a rear end of the inner coil to the core shaft on a front side of the outer rear end joint.

BRIEF DESCRIPTION OF DRAWINGS

The foregoing and other objects, features, aspects and advantages of the invention will become more apparent from the following detailed description when taken in conjunction with the accompanying drawings.

DESCRIPTION OF EMBODIMENTS

<1> A guidewire in accordance with a first aspect of the invention includes: a core shaft; an inner coil that is formed by winding at least one strand, and surrounds a distal side portion of the core shaft; an outer coil that is formed by winding at least one strand, and surrounds the inner coil and the distal side portion of the core shaft; a flat part in flattened shape, which is provided in the distal side portion of the core shaft, expands in width toward a distal end of the distal side portion, and is in contact with an inner peripheral surface of the inner coil at least at the distal end of the distal side portion; a tip joint that joins a front end of the outer coil and a front end of the inner coil to a distal end of the flat part of the core shaft; an outer rear end joint that joins a rear end of the outer coil to the core shaft; and an inner rear end joint that joins a rear end of the inner coil to the core shaft on a front side of the outer rear end joint.

<2> A guidewire in accordance with a second aspect of the invention is the guidewire of the first aspect described above, having a coil joint that is located between the tip joint and the inner rear end joint, and joins only the outer coil and the inner coil to each other.

<3> A guidewire in accordance with a third aspect of the invention is the guidewire of the first aspect described above, wherein the flat part has a pair of side surfaces extending substantially in parallel to an axial direction of the core shaft, and slidably in contact with the inner peripheral surface of the inner coil.

<4> A guidewire in accordance with a fourth aspect of the invention is the guidewire of the first aspect described above, wherein an average distance between adjacent coils of the strand in the inner coil is shorter than an average distance between adjacent coils of the strand in the outer coil.

<5> A guidewire in accordance with a fifth aspect of the invention is the guidewire of the second aspect described above, wherein the outer coil has an open coiled portion, with coils of the strand spaced from one another, on the front side of the coil joint, and a close coiled portion, with coils of strand substantially in contact with one another, on the rear side of the coil joint.

<6> A guidewire in accordance with a sixth aspect of the invention is the guidewire of the second aspect described above, wherein the outer coil has a radiopaque portion, made up of the strand of a radiopaque material, on a front end side of the outer coil while having a radiotransparent portion, made up of the strand of a radiolucent material, on a rear end side of the outer coil, the radiopaque portion has an open coiled portion, with coils of strand spaced from one another and wound in an open coiled manner, on a front end side portion of the radiopaque portion while having a close coiled portion, with coils of strand being substantially in contact with one another and wound in a close coiled manner, on a rear end side of the radiopaque portion, and the coil joint joins the outer coil with the inner coil in the close coiled portion of the radiopaque portion.

<7> A guidewire in accordance with a seventh aspect of the invention is the guidewire of the sixth aspect described above, wherein the radiotransparent portion is wound in a close coiled state where the coils of the strand are in contact with one another.

<8> A guidewire in accordance with an eighth aspect of the invention is the guidewire of the first aspect described above, wherein the inner coil is a hollow stranded coil formed by stranding a plurality of strands.

<1> In the guidewire in accordance with the first aspect of the present invention, the distal side portion of the guidewire is protected by a flexible coil portion having the double coil structure made up of the inner coil and the outer coil. This flexible coil portion thus comes into contact with a blood vessel wall and the like in the body. Hence damage to a blood vessel and the like can be prevented as much as possible. Further, the rotation followability is improved by the inner coil.

Moreover, a flat part expanding to the inner peripheral surface of the inner coil is provided at the distal side portion of the core shaft. Thereby, the torsional stiffness becomes high, as well as the distal end portion of the guidewire becoming flexible. This makes it safe and easy to change a direction of a catheter at the time of moving the catheter along the guidewire even if the torsional stress acts thereon. At the time of performing such an operation, a load may act on a boundary between the flat part and the rear portion of the flat part in the distal side portion. Even in that case, the load is shared by the inner coil by provision of the inner coil. Accordingly, bending or kinking of the core shaft can be prevented as much as possible.

<2> Also in the second aspect of the invention, the rotation followability is improved by the inner coil. Further, in the second aspect, with the outer coil and the inner coil joined to each other by the coil joint, rotation applied from the proximal side of the core shaft can also be transmitted from the outer coil to the inner coil. Therefore, the rotation followability is further improved.

Moreover, the coil joint only joins the outer coil and the inner coil to each other, and does not connect the core shaft to the coil. Therefore, deterioration in flexibility of the inner coil and the outer coil can be prevented as much as possible, so as to maintain the safety.

<3> In the third aspect of the invention, the flat part has a flattened portion with a pair of side surfaces extending substantially in parallel to the axial direction of the core shaft, and slidably in contact with the inner peripheral surface of the inner coil. Hence the distal end portion of the guidewire is flexible and also has higher torsional stiffness.

Further, even with such a configuration, the pair of the side surfaces of the flat part is not fixed to the inner peripheral surface of the inner coil, and can be slid thereon. Therefore, deterioration in flexibility of the inner coil and deterioration in rotation followability of the inner coil can be prevented as much as possible.

<4> In the fourth aspect of the invention, an average distance between adjacent coils of the strand in the inner coil is shorter than an average distance between adjacent coils of the strand in the outer coil. This can prevent loss of the flexibility of the outer coil. Therefore, the double coil structure made up of the inner coil and the outer coil is flexibly bent, so that a guidewire with high safety can be provided.

<5> In the fifth aspect of the invention, the outer coil has the open coiled portion, with the coils of the strand spaced from one another, on the front side of the coil joint. This leads to further improvement in flexibility of the distal side portion of the guidewire. It is thus possible to further prevent damage to the blood vessel and the like in the body.

Further, the outer coil is in the close coiled state where the coils of the strand are substantially in contact with one another on the rear side of the coil joint. Therefore, when rotation applied from the proximal side of the core shaft is transmitted from the outer coil to the inner coil, loss of the transmission of the rotation due to the presence of spaces among the coils of the strand can be prevented as much as possible. This leads to further improvement in rotation followability.

<6> In the sixth aspect of the invention, the stiffness increases in the order of the open coiled portion, which is made of the radiopaque material, of the radiopaque portion, the close coiled portion of this radiopaque portion, and the radiotransparent portion made of the radiolucent material. Therefore, the guidewire has a structure with higher flexibility and safety toward the distal end.

Further, the coil joint is located in the close coiled portion, which has intermediate stiffness, of the radiopaque portion. Therefore, the abrupt stiffness change of the guidewire is prevented as much as possible. This can lead to improvement in rotation followability and pushability of the guidewire.

<7> In the seventh aspect of the invention, the coils of strand on the rear side of the coil joint are all wound in a close coiled manner. Therefore, when rotation applied from the proximal side of the core shaft is transmitted from the outer coil to the inner coil, loss of the transmission of the rotation due to the presence of spaces among the coils of the strand can be prevented as much as possible. This leads to further improvement in rotation followability.

<8> In the eighth aspect of the invention, the inner coil is a hollow stranded coil formed by stranding a plurality of strands. The inner coil thus has a structure with high rotation torque transmissibility as well as flexibility. Hence this can lead to further improvement in rotation followability.

The guidewire of the present embodiment will be described with reference to FIGS. 1 to 4. In FIGS. 1 to 4, the right side is the front side (distal side) that is inserted into a body, and the left side is the rear side (base end side, proximal side) that is operated by an operator.

Figure 1:
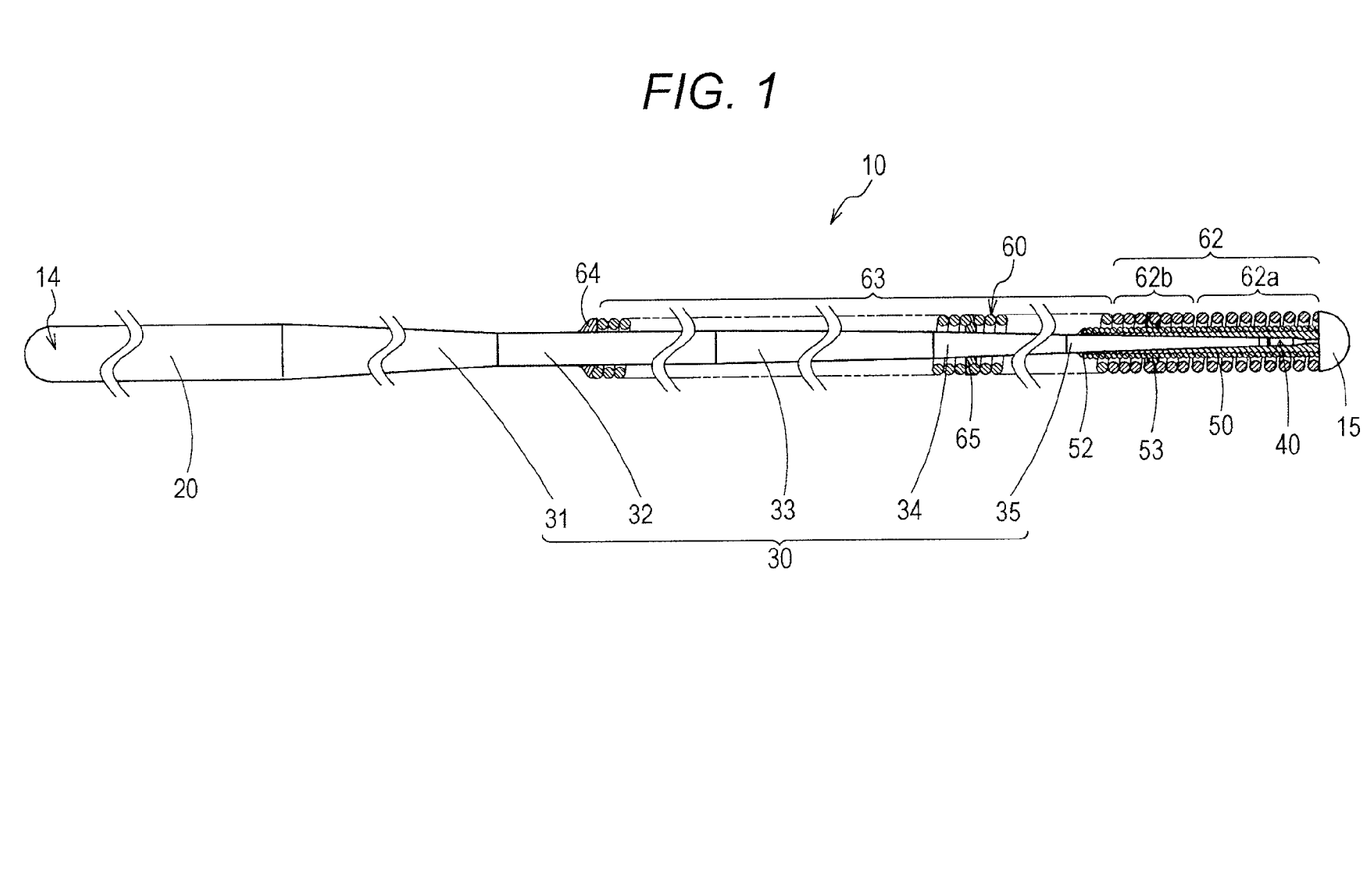
FIG. 1 illustrates an overall view of a guidewire of the present embodiment.

A guidewire 10 is used for treatment of a blood vessel in a brain. The guidewire 10, for example, has a length of about 2000 mm in the case of the present embodiment.

The guidewire 10 mainly includes a core shaft 14, an inner coil 50 and an outer coil 60. The core shaft 14 is roughly divided into a body portion 20, a distal portion 30 and a most distal portion 40. The outer surface of the guidewire 10 from the tip to a predetermined range of the body portion 20 through the outer coil 60 has been subjected to hydrophilic coating.

The distal portion 30 and the most distal portion 40 are portions with a reduced diameter of the core shaft 14, and a total axial length of the both portions is about 420 mm in the present embodiment. The body portion 20 is a portion in cylindrical shape with a given diameter, and takes up the portion other than the distal portion 3C and the most distal portion 40. In the present embodiment, the diameter of the body portion 20 is set to about 0.33 mm.

A material for the core shaft 14 is not particularly limited, but in the case of the present embodiment, stainless steel (SUS304) is used. As the material other than this, a super elastic alloy such as Ni—Ti alloy, a piano wire, or the like may be used.

In the distal portion 30, a first taper part 31, a first small-diameter part 32, a second taper part 33, a third taper part 34, and a fourth taper part 35 are provided in this order from the body portion 20 side toward the most distal portion 40. In the present embodiment, the axial lengths of the first taper part 31 and the first small-diameter part 32 are each about 100 mm.

The first taper part 31 is a tapered portion having a circular cross section. In the present embodiment, a diameter of the first taper part 31 decreases from about 0.33 mm to about 0.20 mm toward a distal direction.

The first small-diameter part 32 is a cylindrical portion having a circular cross section and a given diameter, which is about 0.20 mm in the present embodiment.

The second taper part 33, the third taper part 34 and the fourth taper part 35 are each a tapered portion having a different inclination angle and a circular cross section. In the present embodiment, a total axial length of the second taper part 33, the third taper part 34 and the fourth taper part 35 is about 205 mm. Further, the diameter from the proximal end of the second taper part 33 to a distal end of the fourth taper part 35 is set to decrease from about 0.20 mm to about 0.05 mm.

A cylindrical portion having a given diameter can also be provided among the respective taper parts 33, 34 and 35 as necessary. Further, the number of taper parts and an angle of the taper can also be set as appropriate.

Figure 2:
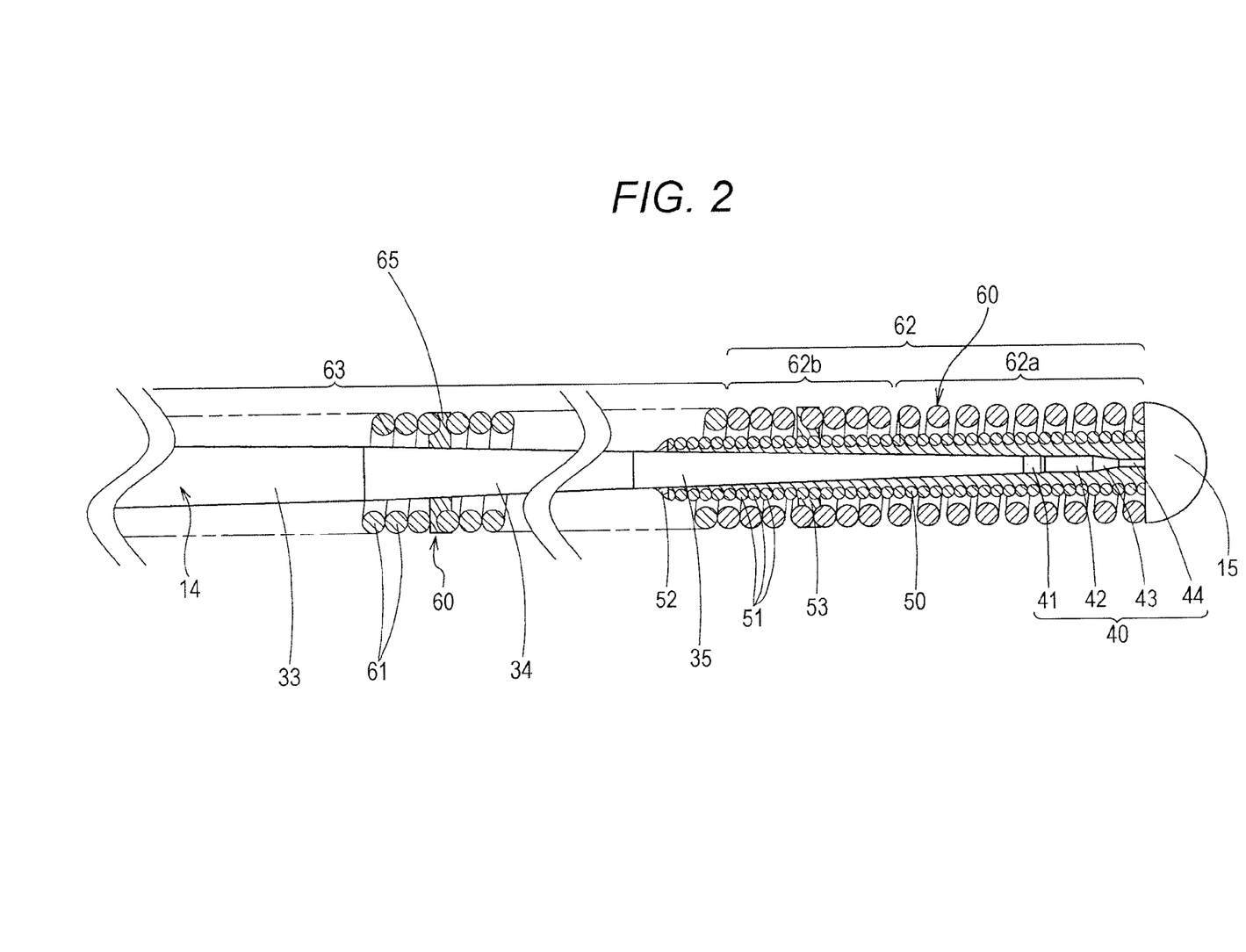
FIG. 2 illustrates a partially expanded view of FIG. 1.

The most distal portion 40 is provided with a large-diameter flexible part 41, a small-diameter flexible part 42, a first flat part 43 and a second flat part 44 in this order from the distal portion 30 side toward the tip. In the present embodiment, the axial length of the most distal portion 40 is about 15 mm.

The large-diameter flexible part 41 and the small-diameter flexible part 42 are cylindrical portions each having a circular cross section and a given diameter. The diameter of the small-diameter flexible part 42 is set smaller than that of the large-diameter flexible part 41. The small-diameter flexible part 42 and the large-diameter flexible part 41 are connected to each other by a minute taper part provided therebetween.

Figure 3:
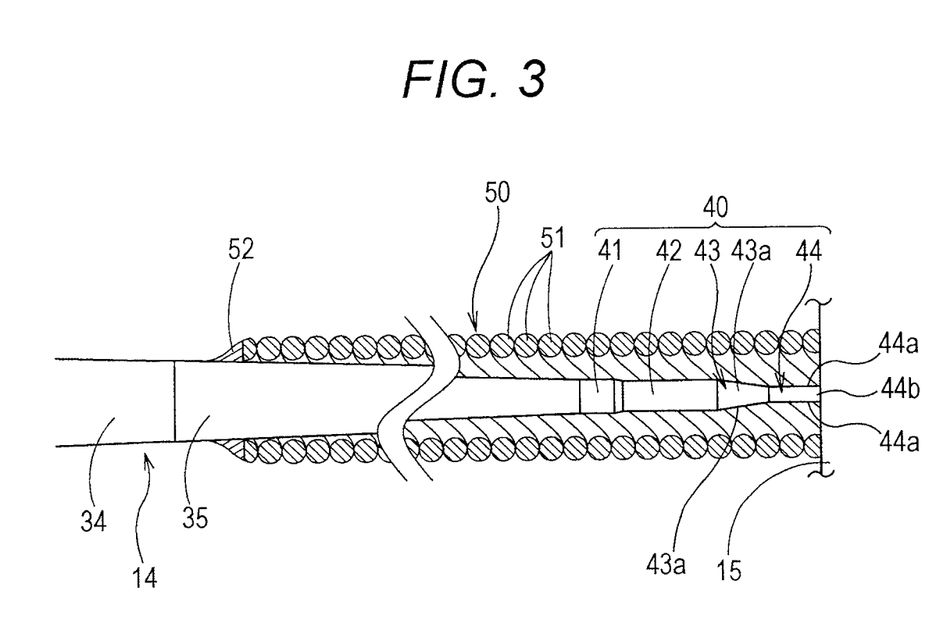
FIG. 3 illustrates a view of a most distal portion of the guidewire of the present embodiment.
Figure 4:
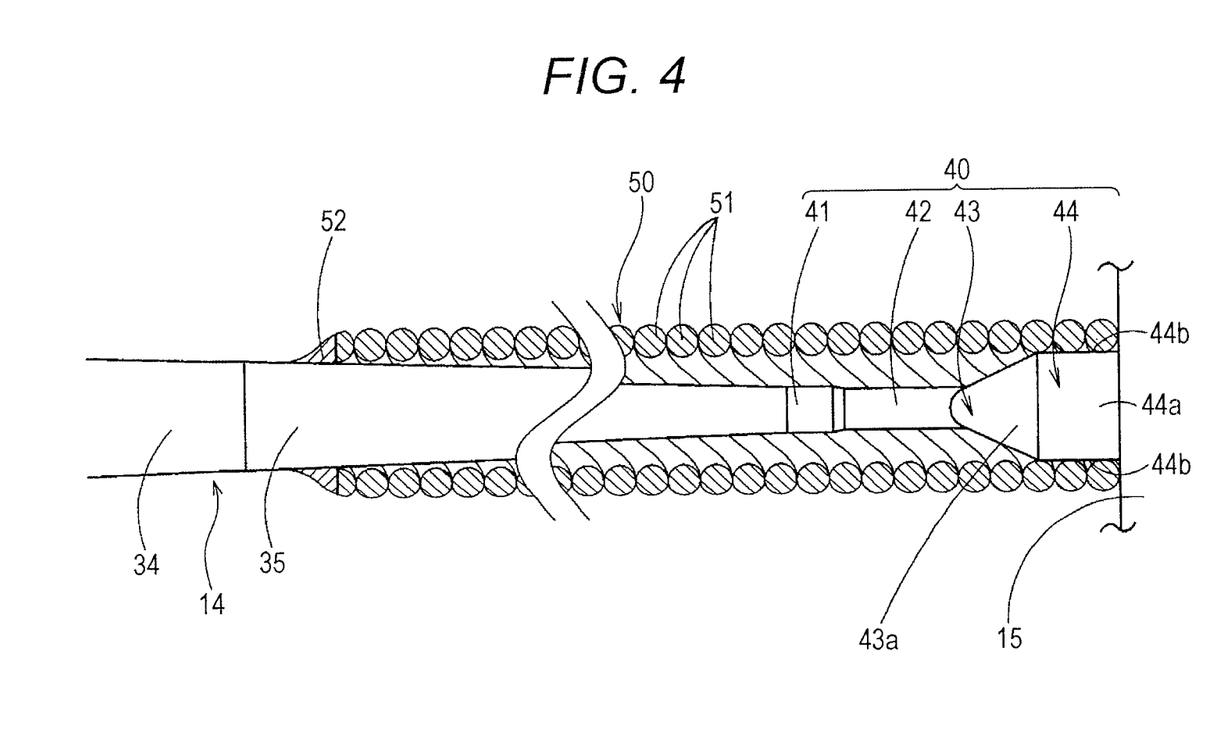
FIG. 4 illustrates a top view of FIG. 3.

The first flat part 43 and the second flat part 44 are portions molded by pressing a cylindrical portion continued from the small-diameter flexible part 42. As illustrated in FIGS. 3 and 4, the first flat part 43 is a tapered portion having a pair of inclined planes 43a with a width increasing, and a thickness in a height decreasing, from the small-diameter flexible part 42 toward the tip side. This first flat part 43 is connected with the second flat part 44 as a flat portion having a substantially rectangular cross section.

The first flat part 43 is provided for modulating a change in stiffness in order to prevent concentration of stress due to an increased change in stiffness between the small-diameter flexible part 42 and the second flat part 44. In the case of the present embodiment, the axial length of the first flat part 43 is about 3.0 mm, so that a sufficiently moderate change in stiffness can be obtained.

As illustrated in FIGS. 3 and 4, the second flat part 44 is a substantially rectangular plate-like portion. The axial length of the second flat part 44 is set substantially the same as the axial length of the first flat part 43. This length is about 3.0 mm in the case of the present embodiment. The second flat part 44 has two pairs of planes 44a and 44b substantially parallel to the axial line of the core shaft 14. Of these, the upper surface 44a is a plane continued to the inclined surface 43a of the first flay part 43. As illustrated in FIG. 4, the side surfaces 44b as a pair of planes substantially orthogonal to the upper surface 44a are in contact with the inner peripheral surface of the inner coil 50, which is described later. That is, the width of the upper surface 44a, which is orthogonal to the axial line of the core shaft 14, is set so as to substantially same as an inner diameter of the inner coil 50. On the other hand, as illustrated in FIG. 3, the upper surface 44a and the inner peripheral surface of the inner coil 50 are spaced from each other by a predetermined distance in a thickness direction of the second flat part 44.

It is to be noted that the second flat part 44 is molded by pressing. For this reason, the side surface 44b is not plane but arc-like in a precise sense. Accordingly, the second flat part 44 having a substantially rectangular cross section includes such a shape with an arc-like side surface.

A total axial length of the first flat part 43 and the second flat part 44 is preferably set to the range of about 2.0 mm to about 10.0 mm. Of the two flat parts, the second flat part 44 constituting the most flexible portion of the core shaft 14 preferably takes up about 1.0 mm or longer.

The flattened portion constituted by the first flat part 43 and the second flat part 44 enhances the torsional stiffness of the tip portion, i.e. the most distal portion 40 of the guidewire 10, as well as making the tip portion more flexible. Further, this flattened portion is also used to angle and direct the tip portion of the guidewire 10, which is called shaping. Herein, shaping would be difficult when this flattened portion is shorter than about 2.0 mm.

Further, as the microcatheter into which the guidewire 10 is inserted, there is often used one having a angled portion at a portion about 8.0 mm from the tip of the catheter. When a total axial length of the first flat part 43 and the second flat part 44 is larger than about 10.0 mm, the flattened portion may be present over the angled portion of the catheter. In such a state, the tip portion of the guidewire 10 is stucked on the front side of the angled portion of the microcatheter. For this reason, when rotational torque is applied from the proximal side of the guidewire 10, torsional stress acts on the guidewire in the stucked angled portion. Further, when further rotational torque is applied and the torsional stress exceeds a given amount, a phenomenon called "whip" may be likely to occur in which the stucked tip portion of the guidewire 10 suddenly moves greatly in a rotating direction to release the torsional stress.

The most distal portion 40 and most of the fourth taper part 35 of the distal portion 30 are inserted through the inside of the inner coil 50. The inner coil 50 is a hollow stranded coil manufactured by stranding a plurality of metal strands 51 on a core, removing residual stress at the time of the stranding by known thermal treatment, and then pulling out the core. In the case of the present embodiment, an outer diameter of the inner coil 50 is about 0.19 mm. Further, the axial length of the inner coil 50 is about 55.0 mm.

Six strands 51 are used for the inner coil 50. A diameter of the strand 51 is about 0.035 mm. A pitch (axial distance defined by one spiral formed by one strand makes a round) of the inner coil 50 is set to be in the range of about 0.25 mm to about 0.29 mm. The number of strands 51 and the diameter thereof are determined as appropriate in view of an outer diameter and stiffness required for the inner coil 50, and are not limited to the above values.

Although a material for the strands 51 is not particularly limited, in the case of the present embodiment, stainless steel is employed. As a material other than this, a super elastic alloy such as an Ni—Ti alloy is used. Further, strands made of different materials may also be combined.

The front end of the inner coil 50 is joined by brazing to the tip of the core shaft 14 with the axial line of the core shaft 14 at the center, with the front end of the outer coil 60. This brazed portion forms a substantially hemispherical tip plug (tip joint) 15. At this time, as the axial length of the second flat part 44, the foregoing length of about 3.0 mm is ensured. Further, the side surface 44b of the second flat part 44 is in contact with the inner peripheral surface of the inner coil 50, but is not brazed thereto. Therefore, the portion of about 3.0 mm at the tip of the inner coil 50 is also in a slidable state where minute relative rotation is allowed between the second flat part 44 and the inner coil 50. This can prevent loss of the flexibility of the inner coil 50.

The rear end of the inner coil 50 is joined by brazing to the fourth taper part 35 of the distal portion 30. This brazed portion forms an inner rear end joint 52.

The inner coil 50 surrounds most of the fourth taper part 35 of the core shaft 14. That is, the inclination angles are different between the third taper part 34 without the inner coil 50 and the fourth taper part 35 with the inner coil 50. This is designed for the purpose of preventing a sudden change in stiffness of the guidewire 10, which is caused by disposing the inner coil 50. That is, changing the inclination of the fourth taper part 35 of the core shaft 14 offsets an increase in stiffness due to the inner coil 50 as much as possible.

Most of the portion from the most distal portion 40 to the first small-diameter part 32 of the distal portion 30, including the inner coil 50, is inserted through the inside of the outer coil 60. The outer coil 60 is formed by winding one metal strand 61. In the case of the present embodiment, an outer diameter of the outer coil 60 is about 0.36 mm. Further, the axial length of the outer coil 60 is about 300.0 mm.

The strand 61 of the outer coil 60 is one strand formed by joining a radiopaque metal wire such as platinum alloy with a radiolucent metal wire such as stainless steel. In the case of the present embodiment, a diameter of the strand 61 is about 0.065 mm. Therefore, in the case of the present embodiment, there is a space of about 0.02 mm in a radial direction between the inner peripheral surface of the outer coil 60 and the outer peripheral surface of the inner coil 50.

The outer coil 60 is formed of one strand. Since a pitch of the outer coil 60 can thereby be approximated to the diameter of the strand, the pitch is about 0.065 mm. On the other hand, the pitch of the inner coil 50 is set to the range of about 0.25 mm to about 0.29 mm as described above. Consequently, an average distance between adjacent strands in the six strands constituting the inner coil 50 is in the range of about 0.042 mm to about 0.048 mm. Hence the average distance between the adjacent coils of the strands of the inner coil 50 is set smaller than the average distance between the adjacent coils of the single strand of the outer coil 60.

In this manner, the inner coil 50 and the outer coil 60 are independent from each other with a space therebetween. The average distance between the adjacent coils of the strands of the inner coil 50 is set smaller than the average distance between the adjacent coils of the single strand of the outer coil 60. This prevents loss of the flexibility of the outer coil. Therefore, the double coil structure made up of the inner coil 50 and the outer coil 60 is easy to bend and flexible.

The portion of the outer coil 60 which is made of the radiopaque metal wire is a portion about 50.0 mm from the front end of the outer coil 60, and constitutes a radiopaque portion 62 that functions as a marker. In the radiopaque portion 62, a portion about 30.0 mm from the front end of the outer coil 60 is an open coiled portion 62a with the coils of the strand 61 wound in an open coiled manner so as to form a space therebetween. A portion in the rear side of the open coiled portion 62a is a close coiled portion 62b with the coils c=the strand 61 wound a close coiled manner so as to come into substantially contact with one another without a space therebetween. The space between coils of the strand 61 in the open coiled portion 62a is about 0.01 mm to about 0.02 mm.

The portion made up of the radiolucent metal wire takes up the portion of the outer coil 60 which is on the rear side of the radiopaque portion 62, and is a radiotransparent portion 63 where coils of the strand 61 are wound in the close coiled manner so as to come into substantially contact with one another.

The front end of the outer coil 60 is joined by brazing to the tip of the core shaft 14 in the tip plug 15, coaxially with the inner coil 50. The rear end of the outer coil 60 is joined by brazing to the first small-diameter part 32 of the distal portion 30. This brazed portion forms an outer rear end joint 64.

Further, the outer coil 60 is joined by brazing to the third taper part 34 of the distal portion 30. This brazed portion forms an outer intermediate joint 65.

The outer coil 60 and the inner coil 50 are joined to each other by brazing in a coil joint 53. The coil joint 53 serves to join only the outer coil 60 and the inner coil 50 to each other. The material for brazing does not reach the core shaft 14, so the inner coil 50 and the core shaft 14 are not joined by the coil joint 53.

The coil joint 53 is located on the rear side of the open coiled portion 62a with the strand 61 wound in the open coiled manner in the radiopaque portion 62 of the outer coil 60, and disposed substantially at the center of the close coiled portion 62b with the strand 61 wound in the close coiled manner. The reason for this is to prevent, as much as possible, an abrupt change in stiffness of the guidewire 10 due to the coil joint 53. That is, in the outer coil 60, the radiopaque portion 62 made up of the radiopaque metal wires such as the platinum alloy has low stiffness as compared with the radiotransparent portion 63 made up of the radiolucent metal wires such as the stainless steel because of the difference in material therebetween. Further, in using the same material, the open coiled portion 62a with the coils of the strand 61 having a space therebetween has lower stiffness than the close coiled portion 62b. Accordingly, the open coiled portion 62a has the lowest stiffness (is most flexible), the close coiled portion 62b has the second lowest stiffness, and the radiotransparent portion 63 with the radiolucent strand 61 wound in the close coiled manner has the highest stiffness. If the boundaries of the portions 62a, 62b and 63 that occur stiffness change are gathered at the coil joint 53, the change in stiffness is further emphasized. Therefore, the above arrangement has been adopted for preventing such emphasized stiffness change as much as possible.

Similarly, the inner rear end joint 52 of the inner coil 50 described above is also disposed on the rear side of the radiopaque portion 62 of the outer coil 60 so as not to be gathered at the boundaries of the portions 62a, 62b and 63 where the change in stiffness occurs.

Further, the close coiled portion 62b of the radiopaque portion 62 and the radiotransparent portion 63, which are located on the rear side of the coil joint 53, are both made up of the close coiled manner of the strand 61. Rotational torque on the proximal side of the guidewire 10 is transmitted to the inner coil 50 not only from the core shaft 14 but also from the outer coil 60 through the coil joint 53. In the above configuration, the strand 61 is closely wound, thereby to prevent loss of transmission of the rotational torque.

Figure 5:
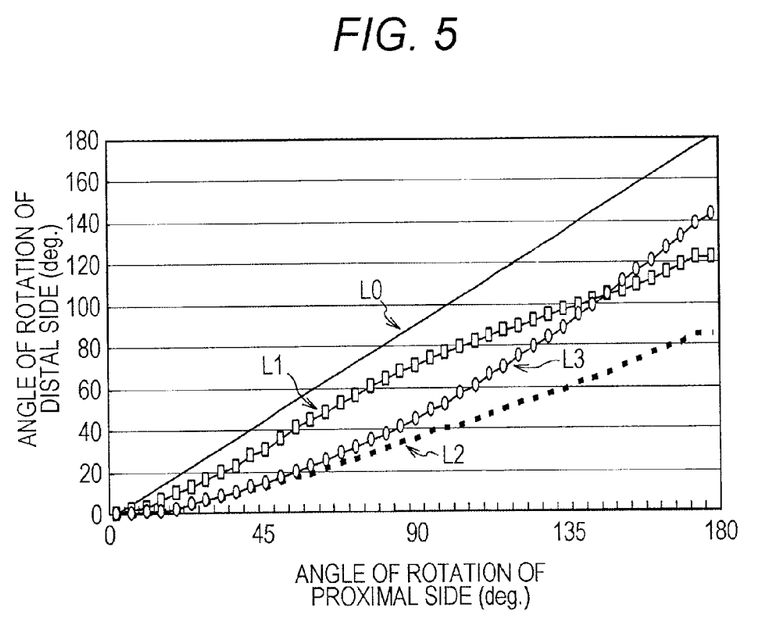
FIG. 5 illustrates a graph of rotation followability of the guidewire of the present embodiment.

For the sake of comparison, three kinds of guidewires were produced, to study an effect exerted by the inner coil 50 and the coil joint 53 that joins the inner coil 50 and the outer coil 60 to each other on the rotation followability. FIG. 5 illustrates a graph of a result thereof. That is, this graph is a result of measuring an angle of rotation of the distal side in the case of rotating the proximal side of each of the three guidewires for test by a measurement device 80 illustrated in FIG. 6, and comparing the guidewires in terms of rotation followability.

Figure 6:
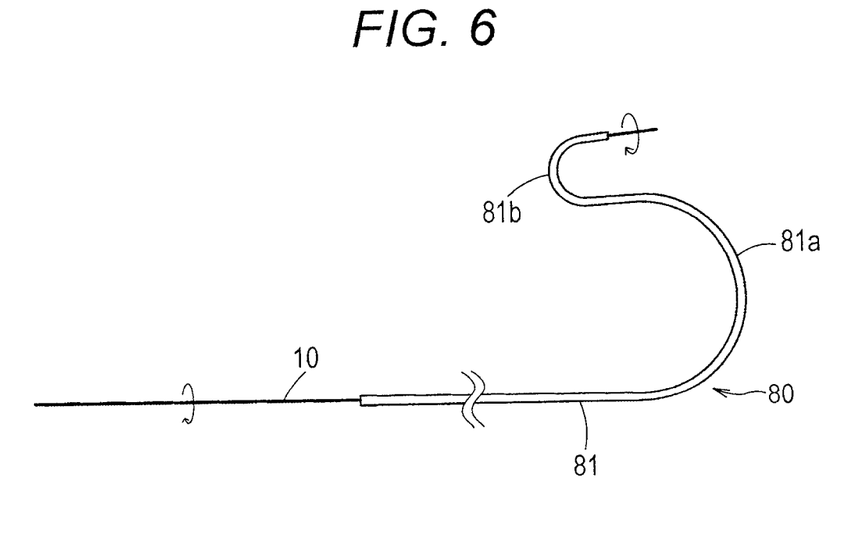
FIG. 6 illustrates a view of a data measurement device of FIG. 5.

The measurement device 80 is formed in a model of a microcatheter that is used simultaneously with the guidewire 10 of the present embodiment, and made up of a resin-made tube 81 having a lumen inside. The tube 81 has a first curved portion 81a with a curvature radius of 60.0 mm on the rear side, and also has a second curved portion 81b with a curvature radius of 10.0 mm on the front side. Inside the measurement device 80 with this configuration, the guidewire produced for test was inserted. The proximal side of each of those was then rotated clockwise by a predetermined angle [degree] up to 180 degrees, and an angle [degree] of rotation on the distal side at that time was measured.

In FIG. 5, a graph L0 indicated by a solid line indicates an ideal line for a guidewire with the proximal side and the distal side thereof rotated in the relation of 1:1. A graph L1 indicated using white rectangles is a measurement result of the test guidewire which is similar to the guidewire 10 of the present embodiment. A difference between the test guidewire and the guidewire 10 is that in the test guidewire, the side surface 44b of the second flat part 44 provided at the tip portion of the core shaft 14 is not in contact with the inner surface of the inner coil 50, but a predetermined space is provided therebetween. This is intended to eliminate the influence exerted by the side surface 44b of the second flat part 44 being in contact with the inner coil 50.

A graph L2 indicated using a broken line is a measurement result of a first comparative guidewire with the configuration of the test guidewire regarding L1 without the inner coil 50. A graph L3 indicated using white circles is a measurement result of a second comparative guidewire with the configuration of the test guidewire regarding L1 only without the coil joint 53 that joins the outer coil 60 and the inner coil 50 to each other.

The guidewire 10 of the present embodiment is aimed, for example, at the use for a blood vessel in a brain. It was found as a result of a study conducted by the present inventors that in the case of being used with the aim as described above, the guidewire is often subjected to the rotating manipulation in the range near 0 to 90 degrees, and the rotation followability in this range is particularly important. For example, in the case of using the guidewire for the brain, at the time of the guidewire entering the inside of a target aneurysm, a highly accurate rotating manipulation is required in the range near 0 to 90 degrees for directing the tip of the guidewire to an opening of the aneurysm.

In FIG. 5, the graph L2 for the first comparative guidewire without the inner coil 50 is far off the ideal graph L0 not only in the range near 0 to 90 degrees but also in the range up to 180 degrees.

As indicated in the graph L3, the second comparative guidewire, provided with the inner coil 50 but without the coil joint 53, has the inner coil 50, and the rotation followability is thereby improved more than the first comparative guidewire. However, it is far off the ideal graph L0 in the range near 0 to 90 degrees. That is, this graph L3 indicates that, when the operator rotates the proximal side of the guidewire, the distal side is not immediately rotated despite transmission of the rotation by the inner coil 50, and the second comparative guidewire thus has inferior operability since a considerable amount of additional rotation of the proximal side is required in order to obtain a desired amount of rotation of the distal side.

On the contrary, as indicated in the graph L1, it is found that the graph L1 of the test guidewire having substantially the same configuration as the guidewire 10 of the present embodiment has the rotation followability slightly inferior to that of the second comparative guidewire in the range after about 130 degrees, but has the rotation followability close to that of the ideal graph L0 in the range near 0 to 90 degrees. That is, in the test guidewire, the distal side is immediately rotated when the operator rotates the proximal side. Hence the graph L1 indicates that the test guidewire has good operability. As described above, it is considered that the factor of improvement in rotation followability of the inner coil 50 is that the rotation from the proximal side of the guidewire 10 to the inner coil 50 is transmitted not only from the core shaft 14 but also from the outer coil 60 through the coil joint 53.

The action of the guidewire 10 of the present embodiment which has the foregoing configuration in the case of being used in an operation for a brain will be described based on FIG. 7.

The guidewire 10 is inserted from a femoral region or the like into an artery, passes through a cervical region, to reach an aneurysm 300 as a target region for treatment which is present in an artery 301 inside a brain. In this process, the guidewire 10 is used in combination with a microcatheter 200. At this time, the tip of the guidewire 10, in the state of being slightly projected from the tip of the microcatheter 200, is allowed to proceed just by a predetermined distance. Thereafter, to follow this tip, the microcatheter 200 is allowed to proceed. Upon reaching the vicinity of the tip of the guidewire 10 by the tip of the microcatheter 200, the guidewire 10 is again made to proceed by the predetermined distance. This is repeatedly performed, to make both of them come closer to a target position.

At this time, a predetermined portion on the tip side of the guidewire 10 comes into contact with a wall surface of a blood vessel. However, this predetermined portion coming into contact with the blood vessel wall is the flexible coil portion having the double coil structure made up of the inner coil 50 and the outer coil 60. Thereby, damage to the blood vessel can be prevented as much as possible.

That is, the outer coil 60 and the inner coil 50 are joined to each other only by the coil joint 53. Therefore, the coils 50 and 60 are independent from each other with a space provided therebetween. Hence the flexibility of each of the coils 50 and 60 is not lost.

In particular, the inner coil 50 is a stranded coil made up of a plurality of strands 51. The guidewire 10 thus has a characteristic of being flexible, as well as a characteristic of being able to realize high rotation followability. In the guidewire 10, the inner coil 50 is joined only to the outer coil 60 by the coil joint 53 except that both end portions of the inner coil 50 are joined to the core shaft 14. That is, the intermediate portion of the inner coil 50 is not joined to the core shaft 14. Further, in the front portion of the inner coil 50, the side surface 44b of the second flat part 44 provided at the tip portion, i.e. the most distal portion 40, of the core shaft 14 is in contact with the inner surface of the inner coil 50. However, these are not fixed to each other, but in the state of allowing minute relative rotation. With such a configuration, loss of the flexibility of the inner coil 50 can be prevented as much as possible. Therefore, the safety can be maintained, while the rotation followability as the characteristics of the stranded coil is enhanced.

As described above, the guidewire 10 prevents the change in stiffness of the core shaft 14 due to the inner coil 50. Further, the guidewire 10 has the structure to prevent, as much as possible, occurrence of abrupt stiffness change, in view of the positional relation between the boundaries of the portions 62a, 62b and 63 and the inner rear end joint 52 and the coil joint 53 of the inner coil 50 because the stiffness of the portions 62a, 62b and 63 changes depending on the material constituting the outer coil 60 and depending on whether the coil is open coiled or close coiled are located. The guidewire 10 is thus provided with high rotation followability. Further, the pushability, which is the easiness to insert the guidewire 10 into the body in the axial direction, is also improved. That is, the guidewire 10 does not have the portion where the stiffness abruptly changes. For this reason, when the guidewire 10 is operated on the proximal side and torque is applied to the guidewire 10, stagnation of transmission of the torque in the stiffness changing portion to cause deterioration in operability can be prevented as much as possible.

Figure 7:
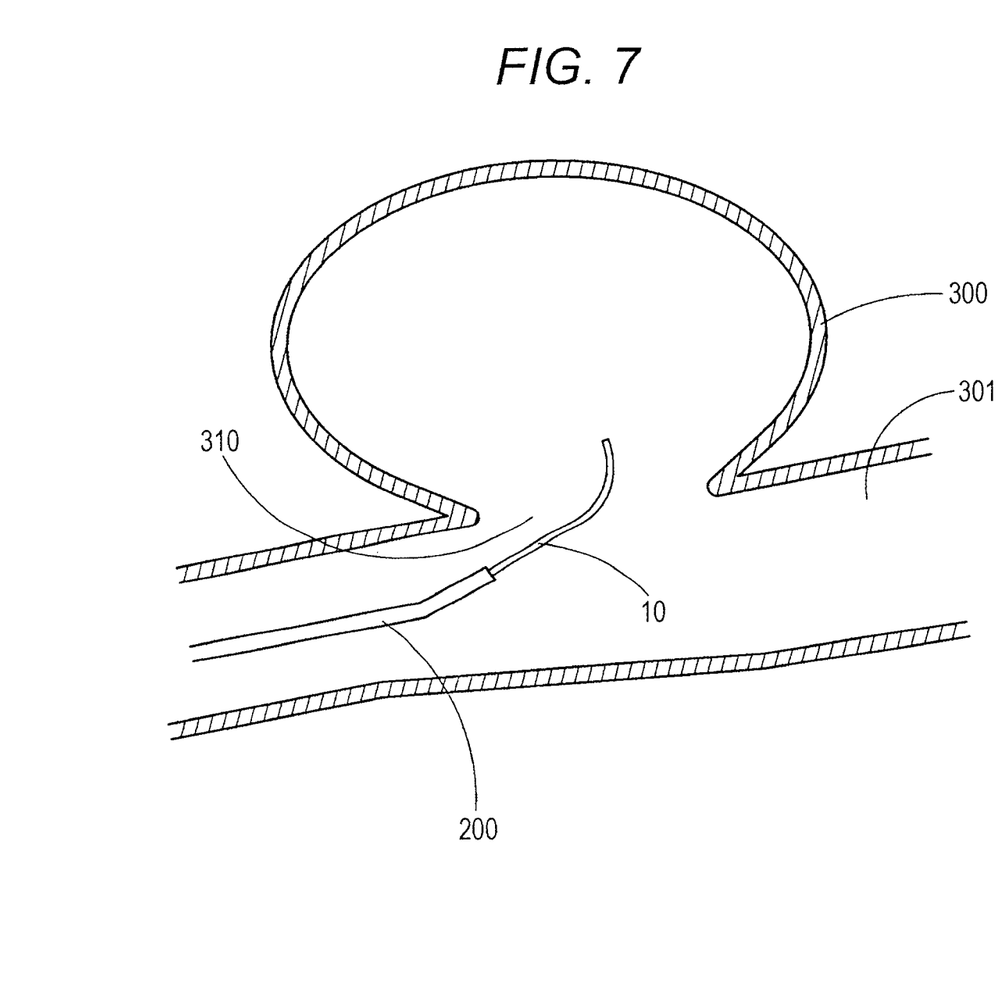
FIG. 7 illustrates an explanatory drawing of an action of the guidewire of the present embodiment.

As schematically illustrated in FIG. 7, when the tip of the guidewire 10 is located in the vicinity of the aneurysm 300 inside the brain as the target region, an operation to insert the tip of the guidewire 10 toward the inside of the aneurysm 300 is performed so that the tip of the microcatheter 200 is allowed to enter the aneurysm 300. Generally, an angle is formed in the tip portion, usually the most distal portion 40, of the guidewire 10 by the conditioning, called shaping, to bend part of the tip portion of the guidewire 10 for forming an angle. This portion formed with the angle is rotated so as to be turned in the direction in which an opening 310 of the aneurysm 300 is present, and then enters the aneurysm 300. In this shaping, bending force is normally applied on the tip portion of the guidewire 10 from a direction orthogonal to the planes of the first flat part 43 and the second flat part 44. Thereby, this tip portion is bent to form an angle. The bent portion is different depending on the operation, but is generally in the range of the second flat part 44 to the fourth taper part 35 where the inner coil 50 is provided.

The tip of the guidewire 10 is directed toward the opening 310 of the aneurysm 300, after which the operation to insert the tip of the guidewire 10 inside the aneurysm 300 is performed with deliberation. As obvious from the characteristics illustrated in FIG. 5 described above, the guidewire 10 of the present embodiment indicates high rotation followability in the range near 0 to 90 degrees. Hence a delicate rotating manipulation on the proximal side of the guidewire 10 by the above operation is effectively transmitted to the distal side of the guidewire 10. It is thereby possible to facilitate this operation. Such effective transmission of the rotating manipulation is realized because the rotation torque from the outer coil 60 can be effectively transmitted to the inner coil 50 by joining the outer coil 60 and the inner coil 50 by the coil joint 53. Moreover, this effect is further enhanced by totally close-coiling the strands 61 of the outer coil 60 on the rear side of the coil joint 53.

In this operation, the tip portion of the guidewire 10 is rotated as described above, to turn the tip of the guidewire 10 in a desired direction. Thereafter, the microcatheter 200 is pushed ahead along the guidewire 10, to change the direction of the tip portion of the microcatheter 200. With the most distal portion 40 of the guidewire 10 provided with the first flat part 43 and the second flat part 44, the torsional stiffness is enhanced. This can facilitate the change in direction of the tip portion of the microcatheter 200. That is, when the microcatheter 200 is proceeded, torsional stress acts in between the tip portion of the guidewire 10 inserted inside the aneurysm 300 and the microcatheter 200. However, the width of the second flat part 44 is widened to the side surface 44b comes into contact with the inner surface of the inner coil 50, whereby the torsional stiffness of the guidewire 10 has been enhanced as much as possible. This enables the microcatheter 200 to smoothly proceed along the guidewire 10, and the direction of the microcatheter 200 to change. Further, even with the width of the second flat part 44 widened as described above, the side surface 44b is not fixed to the inner coil 50. This allows minute relative rotation. Further, the first flat part 43 for moderating the change in stiffness is provided on the rear end side of the second flat part 44. Accordingly, even when a large load acts on the tip portion of the guidewire 10 for changing the direction of the microcatheter 200, the most distal portion 40 of the core shaft 14 can be prevented as much as possible from being bent or kinked.

Moreover, the most distal portion 40 of the core shaft 14 is surrounded by the inner coil 50. This enables the inner coil 50 to receive a load that acts on the most distal portion 40 of the core shaft 14. It is therefore possible to further prevent the most distal portion 40 of the core shaft 14 from being bent or kinked.

By the foregoing operation, the microcatheter 200 reaches the target region along the guidewire 10. Thereafter, the guidewire 10 is extracted from the inside of the body, and a treatment with the microcatheter 200 is performed.

In the embodiment described above, the inner coil 50 is configured of the stranded coil made up of the plurality of strands 51. However, the inner coil 50 may also be a single wired coil made up of one strand although the rotation followability is not improved as much as in the case of the stranded coil. Even in the case of the single wired coil, the inner coil 50 is preferably a close coiled coil with adjacent coils of the strand being in substantially contact with each other from the viewpoint of the rotation followability.

The case of using the guidewire 10 for a brain has been described in the present embodiment. However, the guidewire 10 can be used for other organs than a brain, such as a heart.

Further, the number and size such as an outer diameter and an axial length of the taper part constituting the distal portion 30 and the most distal portion 40 and a cylindrical portion with a given outer diameter in the guidewire 10 can be changed as appropriate in accordance with desired stiffness.

Figure 8:
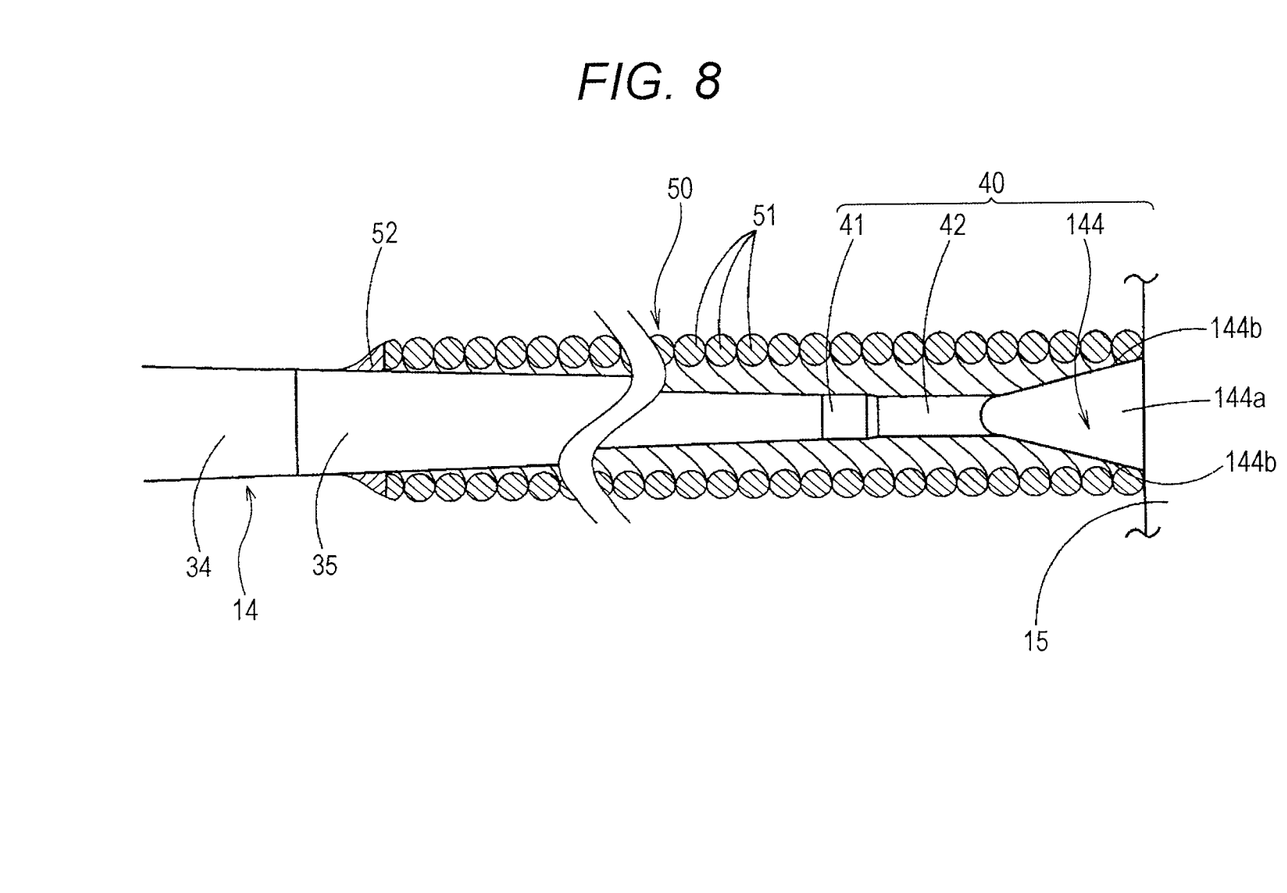
FIG. 8 illustrates a most distal portion of a guidewire of another embodiment.

Moreover, in the embodiment described above, the flat part is formed in combination of the first flat part 43 and the second flat part 44. However, the flat part can take another figure. For example, as illustrated in FIG. 8, the flat part may be a flat part 144 that is made up only of inclined planes 144a and 144b, and spreads to the tip. Also in this case, the flat part 144 is configured such that the distal end of its side surface 144b is in contact with the inner peripheral surface of the inner coil 50, but a portion other than the distal end is not attached to the inner surface of the inner coil 50.

Furthermore, in the embodiment described above, the cross-sectional shape of the second flat part 44 is a substantially rectangular shape. However, this cross-sectional shape may be an oval or elliptical shape as long as it is a flattened shape with a width in substantially contact with the inner surface of the inner coil 50.

Other than these, a variety of figures can be taken as the figure of the most distal portion 40. A variety of figures can be taken, such as a figure formed by combining a plurality of cylindrical shapes with a given outer diameter, and a shape with a plurality of plate-like flat parts each having a substantially rectangular cross section and a thickness that decreases toward the tip.

While the invention has been shown and described in detail, the foregoing description is in all aspects illustrative and not restrictive. It is therefore understood that numerous modifications and variations can be devised without departing from the spirit and scope of the invention.

REFERENCE SIGNS LIST

10 guidewire
14 core shaft
15 tip plug (tip joint)
30 distal portion
40 most distal portion
43 first flat part
44 second flat part
44*b* side surface
50 inner coil
51 strand
52 inner rear end joint
53 coil joint
60 outer coil
61 strand
62 radiopaque portion
62*a* open coiled portion
62*b* close coiled portion
63 radiotransparent portion
64 outer rear end joint
144 flat part

The invention claimed is:

1. A guidewire comprising:
   a core shaft;
   an inner coil that is formed by winding at least one strand, and surrounds a distal side portion of the core shaft;
   an outer coil that is formed by winding at least one strand, and surrounds the inner coil and the distal side portion of the core shaft;
   a flat part in flattened shape, which is provided in the distal side portion of the core shaft, expands in width toward a distal end of the distal side portion, and is in contact with an inner peripheral surface of the inner coil at least at the distal end of the distal side portion of the core shaft so as to form a gap between the inner coil and the outer coil;
   a tip joint that joins a distal end of the outer coil and a distal end of the inner coil to a distal end of the flat part of the core shaft;
   an outer proximal end joint that joins a proximal end of the outer coil to the core shaft;
   an inner proximal end joint that joins a proximal end of the inner coil to the core shaft on a distal side of the outer proximal end joint; and
   a coil joint that is located between the tip joint and the inner proximal end joint, and joins the inner coil to only the outer coil so as to form a gap between the inner coil and the core shaft.

2. The guidewire according to claim 1, wherein the inner coil is a hollow stranded coil formed by stranding a plurality of strands.

* * * * *